United States Patent [19]
Dodd et al.

[11] Patent Number: 5,292,327
[45] Date of Patent: Mar. 8, 1994

[54] SURGICAL KNOT PUSHER

[76] Inventors: Joseph T. Dodd, 5440 Brixton, Sylvania, Ohio 43560; Robert J. Greenler, 29071 Belmont Lake Rd., Perrysburg, Ohio 43551

[21] Appl. No.: 958,661

[22] Filed: Oct. 8, 1992

[51] Int. Cl.⁵ .............................................. A61B 17/00
[52] U.S. Cl. .................................. 606/148; 606/1/139
[58] Field of Search .............. 606/139, 144, 148, 184, 606/187, 205–209

[56] References Cited

U.S. PATENT DOCUMENTS

| | | |
|---|---|---|
| 2,959,172 | 11/1960 | Held . |
| 3,040,747 | 6/1962 | Wood . |
| 3,068,748 | 12/1962 | Schutt et al. . |
| 3,130,727 | 4/1964 | Wood . |
| 3,476,115 | 11/1969 | Graeff et al. . |
| 3,834,395 | 9/1974 | Santos . |
| 4,177,813 | 12/1979 | Miller et al. . |
| 4,328,805 | 5/1982 | Akopov et al. . |
| 4,493,323 | 1/1985 | Albright et al. . |
| 4,602,635 | 7/1986 | Mulhollan et al. . |
| 4,621,640 | 11/1986 | Mulhollan et al. . |
| 4,781,190 | 11/1988 | Lee . |
| 4,836,205 | 6/1989 | Barrett . |
| 4,865,032 | 9/1989 | Jones . |
| 4,898,155 | 2/1990 | Ovil et al. . |
| 4,899,743 | 2/1990 | Nicholson et al. . |
| 4,926,860 | 5/1990 | Stice et al. . |
| 4,957,498 | 9/1990 | Caspari et al. . |
| 5,041,129 | 8/1991 | Hayhurst et al. . |
| 5,059,201 | 10/1991 | Asnis . |
| 5,074,874 | 12/1991 | Yoon et al. . |
| 5,078,721 | 1/1992 | McKeating . |
| 5,080,663 | 1/1992 | Mills et al. . |
| 5,085,661 | 2/1992 | Moss . |
| 5,087,263 | 2/1992 | Li . |
| 5,100,418 | 3/1992 | Yoon et al. . |
| 5,144,961 | 9/1992 | Chen et al. ........................... 606/139 |
| 5,176,691 | 1/1993 | Pierce ................................... 606/148 |

OTHER PUBLICATIONS

General Surgery & Laparoscopy News, p. 14, Aug. 1992, advertisement for Sharpe ENDO ASSIST Endoscopic Knot Pusher, Sharpe ENDOSURGICAL.

Primary Examiner—Stephen C. Pellegrino
Assistant Examiner—Jeffrey A. Schmidt
Attorney, Agent, or Firm—Emch, Schaffer, Schaub & Porcello Co.

[57] ABSTRACT

A surgical knot pusher for moving a knot along a length of suture material to a remote site includes a rod extending along a longitudinal axis from an engagement end to a grasping end, a notch spaced from said engagement end, a passageway sized to receive surgical thread lying on said longitudinal axis and extending from said engagement end to said notch, and a tapered camming surface positioned to be engaged by said surgical thread and moved to a position where it may be grasped by the surgeon.

14 Claims, 4 Drawing Sheets

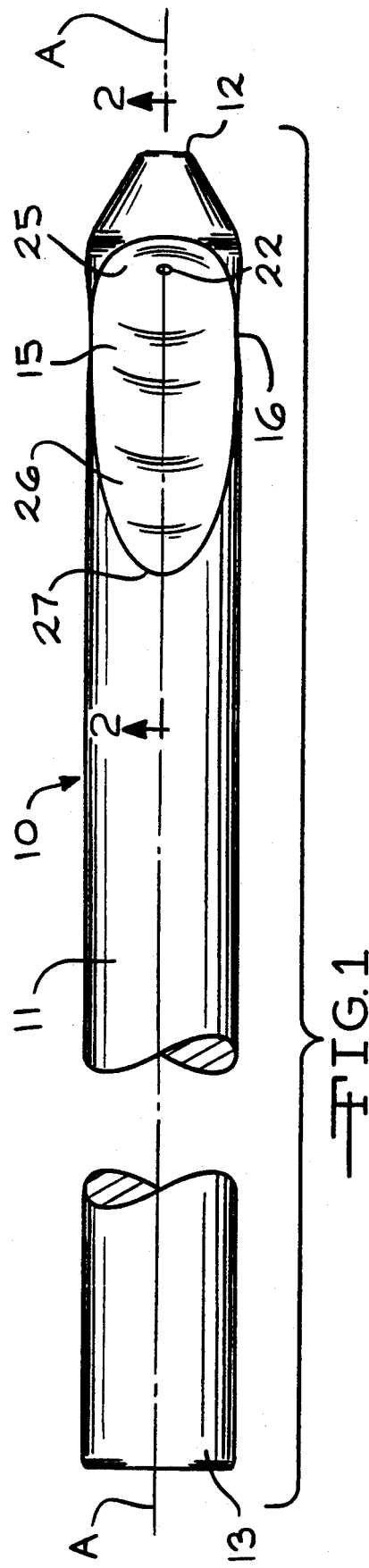
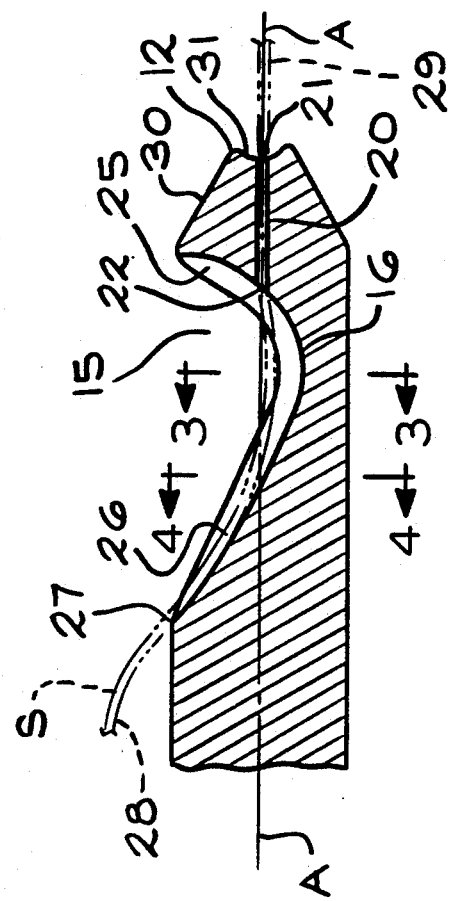
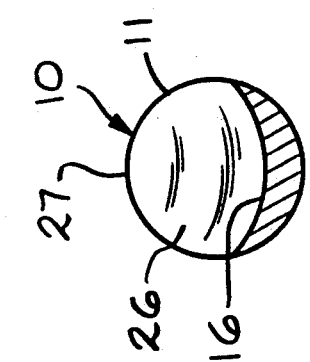
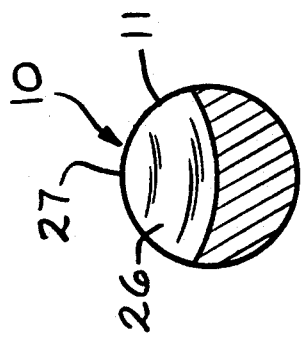

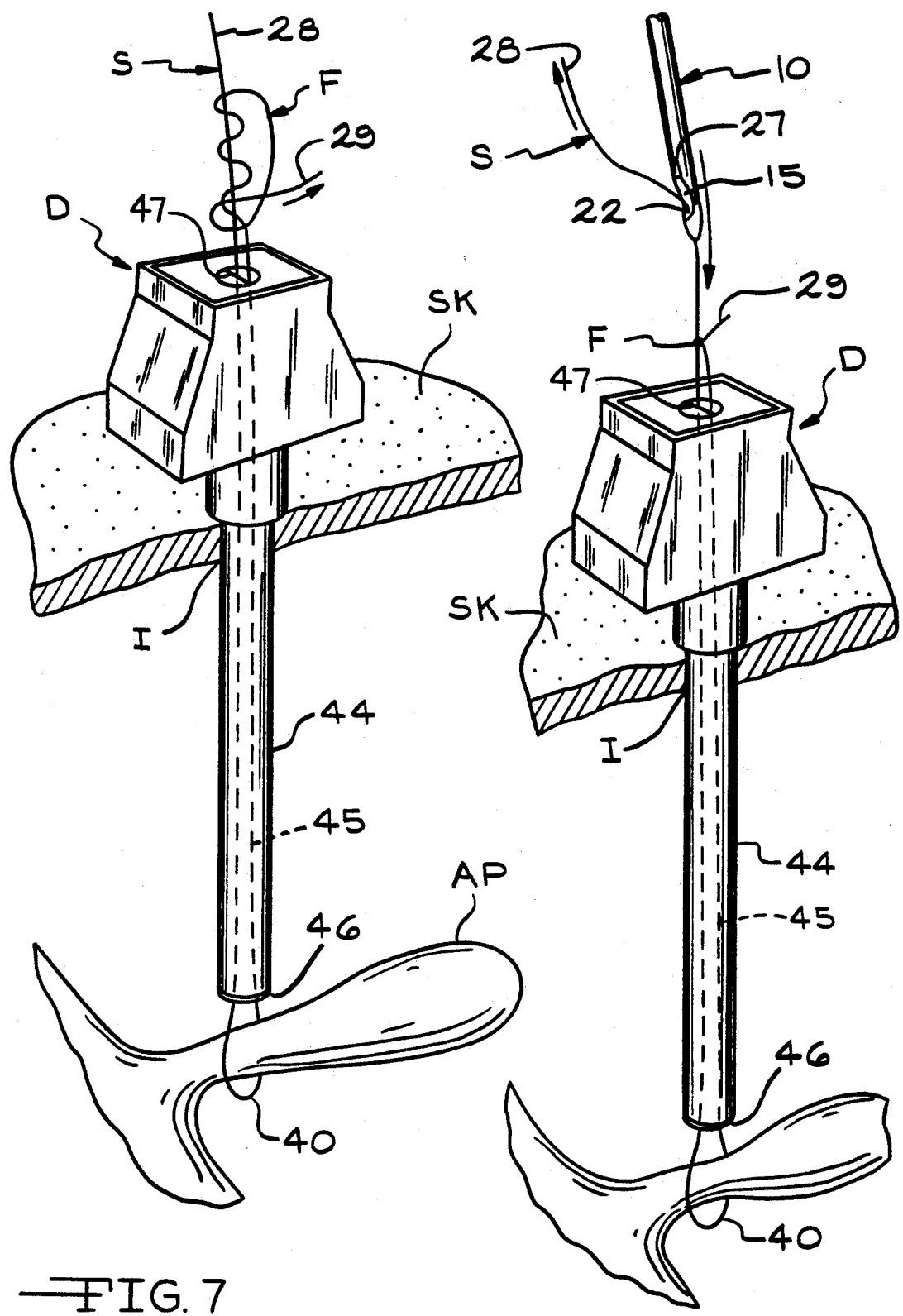

SURGICAL KNOT PUSHER

TECHNICAL FIELD

This invention relates to a surgical knot pusher for moving a knot tied in a length of surgical suture material from a position outside of the body where it was tied to a remote site within a body cavity. It is particularly useful in laparoscopic surgery in which incisions made in the patient are too small to receive the surgeon's hands and the surgical procedures are performed using instruments inserted through the incisions.

DESCRIPTION OF THE PRIOR ART

U.S. Pat. No. 4,602,635 discloses a remote surgical knot tier and method of use which can hold, push and place loops forming a knot in suture material from a knot tying area outside the body to a remote site in the body. The knot tier includes a cylindrical rod member having an angularly cut end with a flat face which is non-perpendicular to the length of the rod member. It has a passage offset from the center of the rod having a size large enough to permit surgical suture material to pass therethrough. The surgical knot tier disclosed in U.S. Pat. No. 4,602,635 is designed for tying knots of a simple overhand type which require that both ends of the suture material remain outside of the body of the patient, with the cylindrical rod member being used to move the knot to the desired site within the body while holding one end of the suture material in tension and holding the other loosely as the rod member is advanced through the cannula. When the rod has been advanced to a position such that the angled end is adjacent the tear at the site thus setting the loop in place, tension is applied to the end which had previously been loosely held to tighten the loop, with the face of the rod member acting as a finger to hold the loop so that it can be tightened and set as part of the knot.

Certain limitations are evident with the surgical knot tier and method disclosed in U.S. Pat. No. 4,602,635. In the first place it is designed to be used with an overhand knot with both ends of the suture material remaining outside of the body during movement of the knot to the desired site. This is significant in that suture material presently used in the United States is provided in standard lengths of 27 inches. Although the remote surgical knot tier disclosed as U.S. Pat. No. 4,602,635 could be used for knee surgery with standard 27 inch lengths of suture material, it would require lengths of suture material longer than 27 inches in order to accommodate both ends remaining outside of the body when performing laparoscopic surgery within the abdominal cavity. Such longer sutures require special orders thereby increasing the cost of such material. Additionally, in the prior art procedure disclosed in U.S. Pat. No. 4,602,635 the rod member must be removed and re-inserted each time a loop is made.

DISCLOSURE OF INVENTION

The present invention relates to a surgical knot pusher specifically designed for use in performing laparascopic surgery including laproscopic surgery deep within the abdominal cavity; however, it is not limited to use in performing such laparoscopic surgery. The surgical knot pusher of the present invention includes a cylindrical rod having a knot-engaging end with a central passageway sized to receive a strand of suture material therethrough but small enough to prevent a knot formed in such suture material to pass therethrough. The central portion of such knot engaging end is tapered or dished inwardly to provide inwardly tapering surfaces to assist in guiding the end of the suture material into the central passageway. Spaced from the knot-engaging end is a notch sufficiently deep to intersect the passageway, thus defining an outlet for such passageway. On the opposite of the notch from the outlet, a wall tapers away from the knot-engaging end and toward the outer periphery of the rod and functions as a camming surface to direct the end of the suture material upwardly from the notch and away from the side of the rod as it is fed through the passageway in order that the surgeon can readily grasp its end. The outer periphery of the knot-engaging end is tapered radially inwardly as it approaches such end in order to permit the surgeon to have good visibility in viewing the knot-engaging end and to permit good maneuverability of the rod throughout the surgical site.

BRIEF DESCRIPTION OF THE DRAWINGS

FIG. 1 is a top plan view of the surgical knot pusher of the present invention.

FIG. 2 is a fragmentary sectional view taken through line 2—2 of FIG. 1.

FIG. 3 is a sectional view taken through line 3—3 of FIG. 2.

FIG. 4 is a sectional view taken through line 4—4 of FIG. 2.

FIGS. 7–10 are schematic perspective views showing the tying of a knot and the pushing of such knot to a surgical site within the body.

BEST MODE OF CARRYING OUT INVENTION

Figure 5:
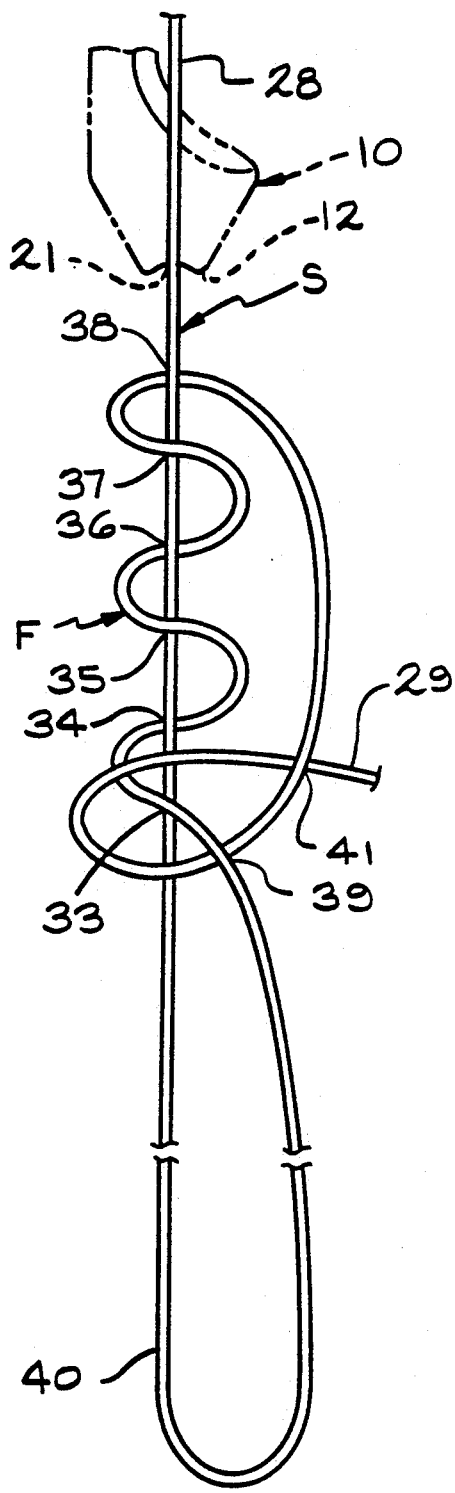
FIG. 5 is a view showing one type of knot which may be pushed to the surgical site using the knot pusher of the present invention.

Referring now to FIGS. 1-4, there is shown a surgical knot pusher 10 comprising an elongated rod 11 extending along an axis A from a first engagement end 12 to a second grasping end 13. The grasping end 13 may be knurled or coated to provide slip resistance. If desired, the grasping end 13 may have an enlarged head for improved gripping.

Preferably, the knot pusher 10 is formed of surgical grade stainless steel or other surgical grade metal or plastic which may be readily sterilized and suitable for surgical use. It may be fabricated from a length of rodding having a cylindrical exterior surface or one having a hexagonal, octagonal or other cross-sectional configuration and having a cross-sectional size permitting its insertion into the body to the surgical site and yet which is sufficiently large to permit ease of grasping by the surgeon. A notch 15 is spaced from the engagement end 12 and extends inwardly from the exterior surface to an area of maximum depth 16 which is below the longitudinal axis A as viewed in FIG. 2, i.e., on the other side of the longitudinal axis A from the portion of the exterior surface from which the notch 15 was formed.

A passageway 20 having a size to readily receive surgical thread or suture material S is positioned on the longitudinal axis A and extends from an inlet 21 at the engagement end 12 to an outlet 22 at the intersection of the passageway 20 with the notch 15.

Surgical suture material comes in a variety of sizes, fine ones having a diameter of 0.005 inch and heavy ones having a diameter of 0.016 inch. Accordingly, knot pushers having different sizes of passageways will be required for use with fine suture material than ones for use with heavy suture material. The diameter of the passageway 20 should be such as to permit suture material S to readily be threaded therethrough but to prevent a knot formed in such suture material to pass therethrough. Preferably, the diameter of such passageway 20 is about twice the diameter of the suture material intended to be used for a given surgical procedure; however, it could be as small as 1.5 times or as large as three times the diameter of such suture material. Thus, for the sizes of suture material customarily used, the diameter of the passageway 20 could be as small as 0.007 inch or as large as 0.048 inch.

As shown in FIG. 2, in longitudinal section, the notch 15 is spoon-shaped and has a forward surface 25 sloping downwardly toward and beyond the axis A and rearwardly away from the engagement end 12 to an area of maximum depth 16 from which extends a camming surface 26 extending upwardly and rearwardly away from the engagement end 12 and passing through the longitudinal axis A to an area of intersection 27 with the exterior surface of the rod 11. As may be seen from FIGS. 3 and 4, both the forward surface 25 and the camming surface 26 are curved in cross-section; however, either or both could be flat in cross-section.

The portion of the knot pusher 10 adjacent the leading end 12 has a conical nose 30 the exterior surface of which is disposed at an angle to the longitudinal axis A of between 30° and 45°. The tapering nose 30 permits the surgeon to have good visibility of the surgical suture material S extending from the inlet 21 of the passageway 20.

The knot pusher 10 also has a concavity encircling the inlet 21 of passageway 20. This concavity is defined by surfaces 31 tapering inwardly toward the axis A and inwardly toward the outlet 22. This concavity provides surfaces 31 which direct the suture material S into the inlet 21 of the passageway 20 and permits ease of threading the suture material into such passageway. This is particularly important in performing laparoscopic surgery as the lights in the operating room are normally dimmed during any such surgery in order that the surgeon can more readily view the television monitor used during such types of surgeries.

In threading the suture material S into the surgical knot pusher 10, the surgeon will feed the surgical suture material into the inlet 21, through the passageway 20 and out of the outlet 22. In continuing to feed the surgical suture material S through the passageway 21, the leading end 28 of the suture material will engage the camming surface 26 and be urged upwardly so that as it passes the area of intersection 27 with the exterior surface it will, due to its inherent stiffness, project upwardly and outwardly from exterior surface of the rod 11 so that the surgeon may readily grasp it.

In FIG. 2, a length of suture material S is shown after being fed to such position with its leading end 28 ready to be pulled further through and its trailing end 29 extending from the inlet 21 available for tying a knot.

Referring now to FIG. 5, there is shown a fisherman's knot F tied in the surgical material S. As may be seen, a length of surgical material S is shown as extending out of the inlet 21 at the leading end 12 of the knot pusher 10 with its trailing end 29 in a position to be tied. The tying is accomplished by initially passing the trailing end 29 over the suture material at area 33, under it at area 34, over it at area 35, under it at area 36, over it at area 37 and under it at area 38. The free end 29 is then carried back under the portion of the loop 40 at area 39 and over the segment between areas 33 and 34, passing under itself in the area 41 to form the fisherman's knot F which may be drawn tight by pulling on the trailing end 29 while applying tension to both the leading end 28 and that portion of the suture material S forming the loop 40. As will be appreciated and as can be readily seen in FIGS. 7-10, the fisherman's knot F is now ready for pushing into the surgical site assume, of course, that the loop 40 has been positioned to encircle the area to be tied off.

Figure 6:
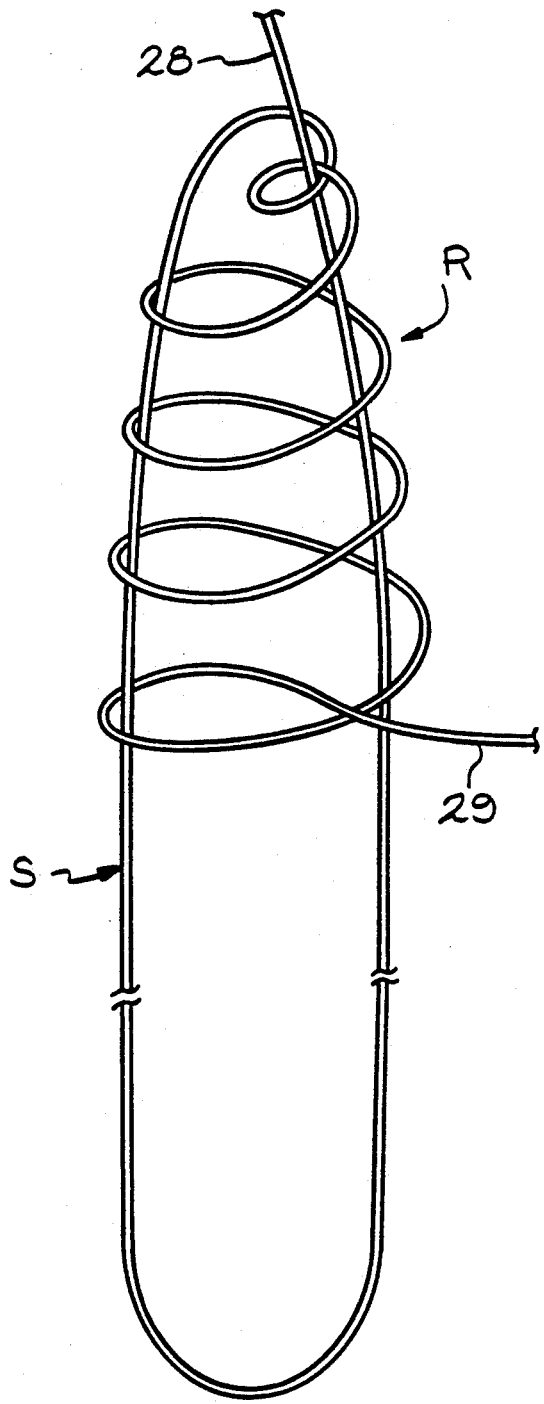
FIG. 6 is a view showing a different type of knot which may be used.
Figures 9, 10:
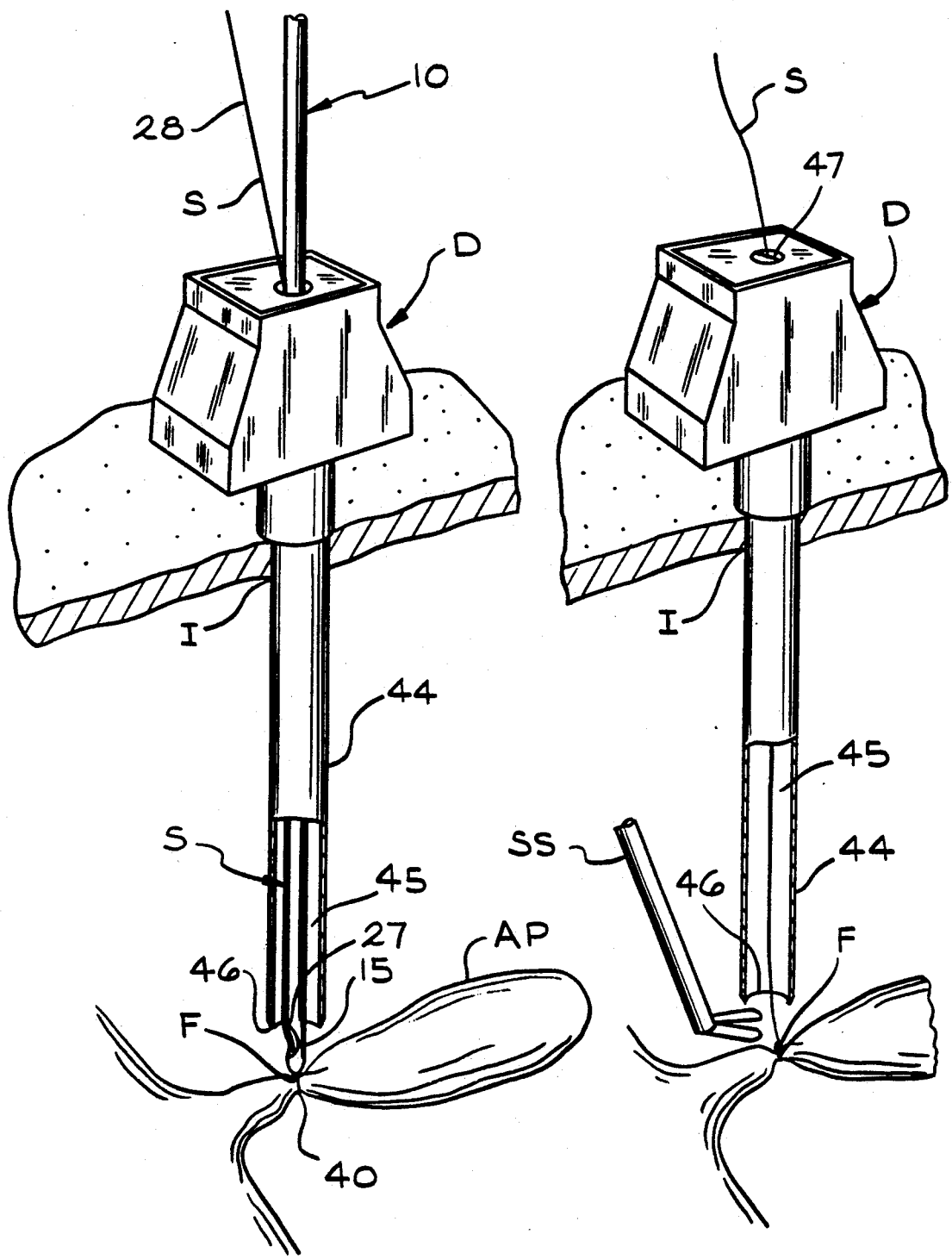

FIG. 6 shows a Roeder Knot R which is another type of knot which may be used with the surgical knot pusher of the present invention. As with the fisherman's knot F, with the Roeder Knot, the trailing end 29 is moved into the surgical site with only the leading end 28 remaining outside of the body of the patient.

Referring now to FIGS. 7-10, there is shown the steps of the procedure used in tying a knot and moving it to the surgical site to tie off an organ or repair a tear or incision.

As shown in such figures, there is provided a combination cannula/inflation device D of a type customarily used in performing abdominal laparoscopic surgery. The device D, for example, may be one sold under the registered trademark AutoSuture® manufactured by U.S. Surgical Company, Norwalk, Conn. The device D in and of itself forms no part of the laparoscopic knot pusher of the present invention; however, it can be used with the method of performing laparoscopic surgery set forth in the method claims. As shown in the figures, the device D has a hollow tube or cannula 44 which may be inserted through a small incision I in the skin SK of a patient. Pressurized gas such as carbon dioxide is introduced through the cannula 44 to open the body cavity of the patient to a position permitting the surgeon to readily view the internal organs including the area intended for the surgical procedures using conventional viewing instruments inserted through a separate incision (not shown) formed in the patient's abdomen. The device D includes a valve 47 for sealing and retaining pressured gas in the body cavity and yet one which may be readily opened to permit insertion of other surgical instruments such as a cutter (not shown) and the knot pusher 10 of the present invention. The device D thus includes a passageway 45 extending through the portion of the device D remaining outside of the skin SK and extending through the cannula 44 to an opening at the outlet end 46 of the cannula 44.

Prior to forming the fisherman's knot F shown in FIG. 7, the trailing end 29 of the suture material is fed through the passageway 45 of the cannula 44 and out of the outlet end 46 where, in cooperation with other instruments inserted through other incisions in the skin SK, it is passed around the organ or area intended to be tied off. In the surgery being performed in FIG. 7, the surgical material S is shown as having a loop 40 formed to tie off an appendix AP of the patient. After forming such loop 40, the trailing end 29 is pulled back through the passageway 44 and out of the device D to a position where such trailing end 29 can be tied into an appropriate knot such as the fisherman's knot F described in connection with FIG. 5. During this procedure, the leading end 28 of the suture remains outside of the body of the patient.

Upon tying the fisherman's knot F, the trailing end 29 is pulled to tighten the knot F and the leading end 28 is then fed into the inlet 21 of the knot pusher 10, through the passageway 20 and out of the outlet 22 to a position where it may be grasped by the surgeon. The knot pusher 10 is then inserted through the valve 47 of the device D, pushing it open in the process, and is inserted through the passageway 45 thereby pushing the fisherman's knot F to the surgical site to tie off the appendix AP from the adjacent organs. Tension is maintained on the leading end 28 of the suture material S by the surgeon in order that the loop 40 may be tightly engaged to tie off the appendix or other organ, with the fisherman's knot F retaining it in such tied off position. Thereafter, the knot pusher 10 is removed from the passageway 45 of the device D and surgical scissors SS, inserted through another incision, cut the suture material S to sever the fisherman's knot F from the rest of the suture material S.

Typically in removing an organ such as the appendix, the procedure will then be repeated to form a second surgical knot slightly spaced from the first and then the organ will be severed by cutting in the area between the two knots so that each severed end is tied off.

The laparoscopic knot pusher and the method of its use disclosed herein provides superior means for performing laparoscopic and other types of surgery requiring the tying off of organs or repair of tears of incisions deep within a body which is superior to those heretofore known.

Many modifications will become readily apparent to those skilled in the art. Accordingly, the scope of the present invention should be determined solely by the scope of the claims appended hereto.

I claim:

1. A surgical knot pusher comprising:
   (a) an elongated rod extending along a longitudinal axis from a first concave engagement end to a second grasping end, said rod having a central longitudinal axis;
   (b) a notch in said rod spaced from said engagement end;
   (c) a passageway in said rod lying on said central longitudinal axis and extending from said engagement end to said notch, said passageway sized to receive a strand of suture material therethrough; and
   (d) a camming surface, in said notch, positioned to be engaged by said suture material as it is fed through said passageway from said engagement end to said notch, said camming surface directing said suture material to a position for grasping.

2. A surgical knot pusher according to claim 1, wherein said rod has a nose portion extending from said engagement end toward said grasping end at an angle such that the included angle between said nose portion and said central longitudinal axis is between 30° and 45°.

3. A surgical knot pusher according to claim 1, wherein said engagement end has a concavity for guiding an end of said suture material into said passageway.

4. A surgical knot pusher according to claim 1, wherein said passageway has a diameter between 0.007 inch and 0.048 inch.

5. A surgical knot pusher according to claim 3, wherein an intersection is defined between said concavity and said engagement end which defines a circle, said circle having a diameter not to exceed 0.100 inch.

6. A surgical knot pusher comprising:
   (a) an elongated rod having an exterior surface and extending along a central longitudinal axis from a first concave engagement end to a second grasping end;
   (b) a notch spaced from said engagement end extending inwardly from said exterior surface to a bottom on the opposite side of said central longitudinal axis;
   (c) a passageway in said rod lying on said central longitudinal axis and extending from said engagement end to said notch, said passageway sized to receive a strand of surgical suture material therethrough; and
   (d) a tapered camming surface, in said notch, positioned to be engaged by said surgical suture material as it is fed through said passageway from said engagement end to said notch, said camming surface tapering away from said engagement end and toward said exterior surface.

7. A surgical knot pusher according to claim 6, wherein said rod has a nose portion extending from said engagement end toward said grasping end at an angle such that the included angle between said nose portion and said central longitudinal axis is between 30° and 45°.

8. A surgical knot pusher according to claim 7, wherein an intersection is defined between said concavity and said engagement end which defines a circle, said circle having a diameter not to exceed 0.100 inch.

9. A surgical knot pusher according to claim 6, wherein said engagement end has a concavity for guiding an end of said suture material into said passageway.

10. A surgical knot pusher according to claim 6, wherein said passageway has a diameter between 0.007 inch and 0.048 inch.

11. A method of tying a length of surgical suture material having a first end and a second end to a body portion at a remote site comprising:
   (a) inserting said first end to said remote site and passing said first end around said body portion while leaving said second end in a position to be manually grasped;
   (b) removing said first end to a position to be manually grasped;
   (c) tying a surgical knot of a type in which one of said ends may be tightened about a length of said suture material and moved along said length;
   (d) providing a knot pusher having
      (i) an elongated rod extending along a central longitudinal axis from a first concave engagement end to a second grasping end;
      (ii) a notch in said rod spaced from said engagement end; and
      (iii) a passageway in said rod lying on said central longitudinal axis and extending from an inlet adjacent said engagement end to an outlet adjacent said notch, said passageway sized to receive said suture material therethrough but preventing movement of said surgical knot therethrough;
   (e) feeding said suture material through said inlet, passageway and said outlet to a position where said surgical knot engages said engagement end and the end of said suture material extending out of said outlet may be manually grasped; and
   (f) pushing said knot pusher with said surgical knot engaged to said engagement end along said length of said suture material to said remote site while applying tension to the other of said ends.

12. A method of tying a length of surgical suture material having a first end and a second end to a body portion at a remote site comprising:
  (a) inserting said first end to said remote site and passing said first end around said body portion while leaving said second end in a position to be manually grasped;
  (b) removing said first end to a position to be manually grasped;
  (c) tying, in said suture material adjacent said first end, a surgical knot of a type in which said first end may be tightened about a length of said suture material and moved along said length;
  (d) providing a knot pusher having
    (i) an elongated rod with an exterior surface extending along a central longitudinal axis from a first concave engagement end to a second grasping end;
    (ii) a notch spaced from said engagement end extending inwardly from said exterior surface; and
    (iii) a passageway in said rod lying on said central longitudinal axis and extending from an inlet adjacent said engagement end to an outlet adjacent said notch, said passageway sized to receive said suture material therethrough but preventing movement of said surgical knot therethrough;
  (e) feeding said second end through said inlet, passageway and said outlet to a position where said surgical knot engages said engagement end and said second end may be manually grasped; and
  (f) pushing said knot pusher with said surgical knot engaged to said engagement end along said length of said suture material to said remote site while applying tension to said second end.

13. A method of tying a length of surgical suture material of predetermined diameter having a first end and a second end to a body portion at a remote site comprising:
  (a) inserting said first end to said remote site and passing said first end around said body portion while leaving said second end in a position to be manually grasped;
  (b) removing said first end to a position to be manually grasped;
  (c) using one of said ends, tying a surgical knot of a type in which said one end may be tightened about a length of said suture material and moved along said length;
  (d) providing a knot pusher having
    (i) an elongated rod extending along a central longitudinal axis from a first concave engagement end to a second grasping end;
    (ii) a notch spaced from said engagement end;
    (iii) a passageway in said rod lying on said central longitudinal axis and extending from an inlet adjacent said engagement end to an outlet adjacent said notch, said passageway sized to receive said suture material therethrough but preventing movement of said surgical knot therethrough;
  (e) feeding the other of said ends through said inlet and passageway to move said suture material to a position where said other end may be manually grasped and said engagement end engages said surgical knot; and
  (f) pushing said knot pusher with said surgical knot engaged to said engagement end along said length of said suture material to said remote side while maintaining said suture material in said passageway and applying tension to the other of said ends.

14. A method of tying a length of surgical suture material of predetermined diameter having a first end and a second end to a body portion at a remote site comprising:
  (a) inserting said first end to said remote site and passing said first end around said body portion while leaving said second end in a position to be manually grasped;
  (b) removing said first end to a position to be manually grasped;
  (c) tying, in said suture material adjacent said first end, a surgical knot of a type in which said first end may be tightened about a length of said suture material and moved along said length;
  (d) providing a knot pusher having
    (i) an elongated rod extending along a central longitudinal axis from a first concave engagement end to a second grasping end;
    (ii) a notch spaced from said engagement end;
    (iii) a passageway in said rod lying on said central longitudinal axis and extending from an inlet adjacent said engagement end to an outlet adjacent said notch, said passageway sized to receive said suture material therethrough but preventing movement of said surgical knot therethrough;
  (e) feeding said second end through said inlet and passageway to move said suture material to a position where said second end may be manually grasped and said engagement end engages said surgical knot; and
  (f) pushing said knot pusher with said surgical knot engaged to said engagement end along said length of said suture material to said remote site while maintaining said suture material in said passageway and applying tension to said second end.

* * * * *